United States Patent [19]

Imran et al.

[11] Patent Number: 4,614,192

[45] Date of Patent: Sep. 30, 1986

[54] IMPLANTABLE CARDIAC DEFIBRILLATOR EMPLOYING BIPOLAR SENSING AND TELEMETRY MEANS

[75] Inventors: Mir Imran; Stanley M. Bach, Jr., both of Pittsburgh; Steve A. Kolenik, Leechburg, all of Pa.

[73] Assignee: Mieczyslaw Mirowski, Owings Mills, Md.

[21] Appl. No.: 478,038

[22] Filed: Mar. 23, 1983

Related U.S. Application Data

[63] Continuation-in-part of Ser. No. 370,191, Apr. 21, 1982, abandoned.

[51] Int. Cl.⁴ ............................................. A61N 1/36
[52] U.S. Cl. ........................ 128/419 D; 128/419 PG
[58] Field of Search ................. 128/419 PG, 419 PT, 128/419 D, 419 PS, 689, 705, 706, 708, 903, 702–704

[56] References Cited

U.S. PATENT DOCUMENTS

| | | | |
|---|---|---|---|
| Re. 27,757 | 9/1973 | Mirowski | 128/419 D |
| 2,202,340 | 5/1940 | Langer et al. | |
| 3,442,269 | 5/1969 | Druz | 128/419 D |
| 3,554,188 | 1/1971 | Lasch et al. | 128/706 |
| 3,572,324 | 3/1971 | Petersen | 128/706 |
| 3,608,545 | 9/1971 | Novack et al. | 128/706 |
| 3,717,140 | 2/1973 | Greenwood | 128/689 |
| 3,804,098 | 4/1974 | Friedman | 128/404 |
| 3,805,795 | 4/1974 | Denniston et al. | 128/419 D |
| 3,810,457 | 5/1974 | Bottcher et al. | 128/2.1 R |
| 3,825,015 | 7/1974 | Berkovits | 128/419 P |
| 3,857,398 | 12/1974 | Rubin | 128/706 |
| 3,882,277 | 5/1975 | DePedro et al. | 128/903 |
| 3,939,824 | 2/1976 | Arneson et al. | 128/708 |
| 3,974,834 | 8/1976 | Kane | 128/418 |
| 3,983,476 | 9/1976 | Konopasek | 128/419 D |
| 4,102,346 | 7/1978 | Fulker | 128/419 PS |
| 4,164,946 | 8/1979 | Langer | |
| 4,181,134 | 1/1980 | Mason et al. | 128/706 |
| 4,184,493 | 1/1980 | Langer et al. | |
| 4,210,149 | 7/1980 | Heilman et al. | 128/419 D |
| 4,223,678 | 9/1980 | Langer et al. | 128/419 D |
| 4,245,641 | 1/1981 | Mann et al. | 128/419 PG |
| 4,259,966 | 4/1981 | Cannon et al. | 128/706 |
| 4,280,502 | 7/1981 | Baker, Jr. et al. | 128/419 PG |
| 4,295,474 | 10/1981 | Fischell | 128/419 D |
| 4,312,356 | 1/1982 | Sowton et al. | 128/419 PG |
| 4,340,063 | 7/1982 | Maurer | 128/421 |
| 4,349,030 | 9/1982 | Belgard et al. | 128/419 PG |
| 4,393,877 | 7/1983 | Imran et al. | |
| 4,407,288 | 10/1983 | Langer et al. | 128/419 D |
| 4,457,315 | 7/1984 | Bennish | 128/704 |
| 4,475,551 | 10/1984 | Langer et al. | 128/419 D |

OTHER PUBLICATIONS

Zelina et al. "A Telemetry Pulse–Frequency Demodulation System Employing Microprocessor Controlled Noise Rejection" *Conference: IEEE 1979 Frontiers of Engineering in Health Care* Denver, Col., USA, pp. 12.5.1–12.5.3.

Stratbucker et al. "Automatic Cardioversion Using Electronic Arrythmia Logic" *Rocky Mountain Eng. Soc.* 1965, pp. 57–61.

*Primary Examiner*—William E. Kamm
*Assistant Examiner*—Mitchell J. Shein
*Attorney, Agent, or Firm*—Fleit, Jacobson, Cohn & Price

[57] ABSTRACT

An implantable cardioversion system employing a bipolar electrode for R-wave sensing, the system utilizing heart rate averaging and probability density function techniques in determining whether or not the heart of a patient is to be automatically cardioverted. An improved bipolar electrode facilitates acquisition of a highly accurate R-wave. The implantable system is further provided with the capabilities of (1) providing, upon magnet-type interrogation, an audible indication of proper placement of the bipolar electrode in the body of a patient, (2) providing an audible indication to verify the status of the implanted device (activated or deactivated), (3) the capability of providing, upon request, a transmitted signal modulated with stored information corresponding to the number of times cardioversion of the patient has taken place, (4) the capability of preventing external cardioversion shock from being shunted across the electrodes, and (5) the capability of detecting average heart rate.

16 Claims, 7 Drawing Figures

IMPLANTABLE CARDIAC DEFIBRILLATOR EMPLOYING BIPOLAR SENSING AND TELEMETRY MEANS

CROSS REFERENCES TO RELATED PATENTS AND PATENT APPLICATIONS

This application is a continuation-in-part of U.S. patent application Ser. No. 370,191 of the same inventors entitled CARDIOVERSION USING BIPOLAR ELECTRODE FOR SENSING filed Apr. 21, 1982 now abandoned, incorporated herein.

FIELD OF INVENTION

This invention relates to an implantable defibrillator device for defibrillating the heart of a patient, but more specifically, to a defibrillating system employing improved arrythmia detection means for more reliably detecting abnormal heart functions and telemetry means for transmitting information indicative of the status and operation of the implanted defibrillator.

DESCRIPTION OF PRIOR ART

In recent years, substantial progress has been made in the development of defibrillating techniques for effectively cardioverting various heart disorders and arrhythmias. Past efforts have resulted in the development of implantable electronic standby defibrillators which, in response to the detection of an abnormal cardiac rhythm, discharge sufficient energy via electrodes connected to the heart to depolarize and restore it to normal cardiac rhythm.

Research efforts have also been directed toward developing techniques for reliably monitoring heart activity in order to determine whether cardioversion is necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in commonly owned U.S. Pat. Nos. 4,184,493 and 4,202,340, both of Langer et al.

A more recent system, as disclosed in commonly owned co-pending application Ser. No. 175,670 of Langer et al filed Aug. 5, 1980, utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate for a variety of different electrocardiogram (ECG) signal shapes. One such system is disclosed in commonly owned co-pending application Ser. No. 263,910 of Imran et al, filed May 15, 1981.

Despite these past efforts and the level of achievement prevalent among prior art devices, there are potential difficulties and drawbacks that may be experienced with such devices. Such difficulties include the following: (1) R-wave detection is still in need of improvement since the ability to detect the R-wave with the utmost accuracy is vital to the proper and efficient operation of the implantable defibrillator device; (2) sometimes the sensing electrode or electrodes which monitor heart activity become displaced or dislodged thus degrading or attenuating completely the sensed ventricular beating signal which thereby causes unreliable or irregular operating cycles of the defibrillator device; (3) once implanted, there presently is no means to determine the status (active or inactive) or other operating condition or function of the implanted defibrillator; (4) since the defibrillator device is intended for automatic operation on an as-needed basis, it would be advantageous to provide means for keeping a running count of the number of defibrillating pulses issued by the defibrillator, and upon interrogation, to transmit the memorized count information and other status information without the need to employ invasive surgery; (5) since a significant problem with defibrillator devices arises when their external high-voltage electrodes are shunted, it would be considered advantageous to provide such implantable defibrillator with an anti-short circuit (anti-shunt) capability to protect sensitive internal circuits and the electrodes; and (6) since there is a danger, when employing conventional defibrillating devices with R-wave asynchronous countershock of accelerating arrythmia, it is advantageous to provide R-wave synchronous cardioversion.

In view of the foregoing, it is an objective of the present invention to provide an implantable defibrillator or cardioversion device having improved sensing means for detecting occurrences of abnormal cardiac rhythms and for automatically issuing defibrillating pulses in response thereto.

Another objective of the present invention is to provide an improved defibrillator or cardioversion system in which proper placement of the rate sensing electrodes can be ascertained without invasive surgery.

A further objective of the present invention is to provide an implantable defibrillator or cardioversion device which, upon interrogation by external means, can transmit various status information indicative of the operating state and proper lodging of electrodes about the heart.

Yet a further objective of the present invention is to provide an implantable defibrillator or cardioversion system in which telemetry information transmitted externally of the patient is encoded and transmitted by circuit elements in the implantable device.

A further objective of the present invention is to provide an implantable defibrillator or cardioversion system having the capability of preventing external defibrillating pulses from being short-circuited across the defibrillating electrodes.

An additional objective of the present invention is to provide an implantable defibrillator or cardioversion system including means to reduce the likelihood of accelerating the patient's arrythmia upon cardioversion.

SUMMARY OF THE INVENTION

In accordance with a comprehensive embodiment of this invention in the attainment of the above-stated and other objectives, a cardioversion system includes an implantable defibrillator and an external non-invasive controller/monitor for altering the state and/or retrieving status information from the implanted defibrillator.

The implantable defibrillator comprises a high-voltage inverter circuit with shunt-prevention means; the combination of a PDF circuit and a heart-rate analysis circuit that each detect abnormal cardiac rhythms and that jointly activate the high-voltage inverter circuit; a series of electrodes connected to the heart including a bipolar sensing electrode coupled with the heart-rate analysis circuit for sensing ventricular beating signals, and high-voltage pulse delivery electrodes coupled with the high-voltage inverter circuit and the PDF circuit for, respectively, delivering high-energy defibrillating pulses and providing PDF information signals; a pulse counter/memory for counting and storing the number of defibrillating pulses issued by the inverter circuit; a piezoelectric speaker coupled to the wall of a case enclosing the defibrillator circuits for generating audible tones indicative of the status of the defibrillator; and means responsive to an external magnet for changing the state of the defibrillator (active or inactive), enabling internal testing functions of the defibrillator and telemetry means for transmitting encoded status information (such as pulse count and capacitor charge-time information) of the defibrillator, and permitting audio tones to be emitted by the piezoelectric speaker, which tones non-invasively indicate the status of the defibrillator and proper placement of the bipolar sensing electrode.

The external controller/monitor includes a handheld magnet for initiating the aforementioned functions by proper placement thereof over a reed switch inside the implanted defibrillator, and an R.F. receiver circuit including a demodulator for decoding and displaying on a display device certain status information electromagnetically transmitted from the implanted defibrillator.

The invention, though, is pointed out with particularity in the appended claims. The above and further objectives and advantages of this invention will be better understood by referring to the following description of an illustrative embodiment of the invention taken in connection with the accompanying drawings.

BRIEF DESCRIPTION OF DRAWINGS

FIG. 6 depicts the 4-count hold circuitry of FIG. 1.

DESCRIPTION OF ILLUSTRATIVE EMBODIMENT

General Description

Figure 1:
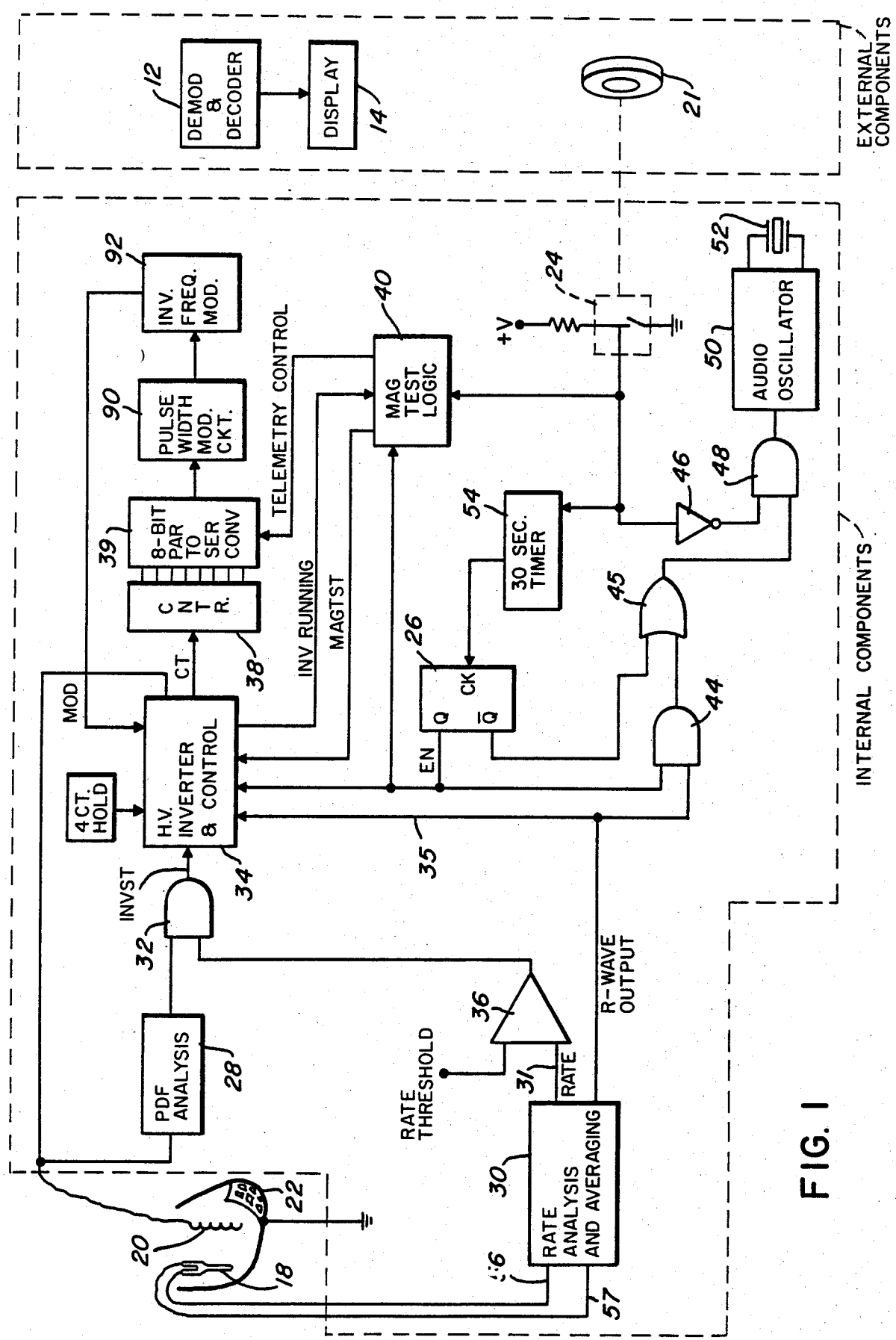
FIG. 1 depicts a simplified block diagram of the internal and external components of the invention.

FIG. 1 depicts, in a functional block-diagram format, the internal and external components of the invention. The implanted components are enclosed in a metallic case (not shown) and constitute the standby defibrillator which detects abnormal cardiac rhythms. In response to the detection of such abnormal cardiac rhythms, the defibrillator issues a series of defibrillating pulses (25 to 30 joules) to the heart 10 of a patient, and thereafter, records in a memory (e.g. counter) an accumulated number of defibrillating pulses issued. In the preferred embodiment, the defibrillator can issue three 25-joule defibrillating pulses followed by a 30-joule pulse if needed. After the initial pulse, re-detection takes place and if the arrythmia is still present, charging is initiated and a second pulse is delivered after completion of the charging cycle. This pattern continues, if necessary, until the fourth high-energy shock is delivered. Thereafter, no further pulses can be delivered until at least 35 seconds of normal sinus rhythm is detected. Then, the device is ready for a further sequence of four shooks.

In the present invention, several electrodes are connected to the patient's heart and the defibrillator circuits. These electrodes carry sensing information from the heart to the defibrillator and deliver the high-energy defibrillating pulses from the defibrillator to the heart. The electrodes include a bipolar sensing electrode 18 adapted to be located in the right ventricle for sensing electrical activity from the ventricular contractions, and transcardiac sensing and high-voltage delivery electrodes 20 and 22 for sensing electrical activity and for delivering the defibrillating pulses. The electrode 20 is adapted to be located in the superior vena cava and the patch electrode 22 is adapted to be connected to the myocardium near the apex of the heart. Their structure and circuit connections are subsequently explained in greater detail, particularly the bipolar sensing electrode 18 as it partly forms a basis of this invention.

The external components of the invention, on the other hand, include a demodulator and decoder circuit 12 which detects RF signals (radio frequency signals) and decodes telemetry data transmitted, in the preferred embodiment, electromagnetically by current-carrying conductors in the implanted defibrillator circuits. Further, a display device 14 displays both the charge-time required for charging a high-voltage energy storage capacitor in the defibrillator and the accumulated pulse-count information stored in the implanted defibrillator. Charge time is derived from detecting RF signals emanating from the h.v. inverter coils in the inverter when it is running while pulse-count information is derived by decoding a modulated transmission of the same RF signals emitted by the h.v. inverter when it is running, as will be discussed below.

With the defibrillator implanted subcutaneously, placing a ring magnet 21 on the skin of the patient in close proximity to a reed switch 24 (enclosed in the case of the defibrillator) does one of three things. First, it permits an audio oscillator 50 to emit acoustic sounds synchronous with the heart beat if the defibrillator is active, and continuous if the defibrillator is inactive. Second, it changes the status of a status flip-flop 26 if the magnet is held in place more than a predetermined time period (e.g., 30 seconds). Third, upon transient application of the magnet 21, when the defibrillator device is in the active state, it initializes the defibrillator to transmit telemetry data of pulse count information and capacitor charge-time information. These operations also are subsequently described in greater detail.

As previously stated, another attribute of the implantable defibrillator is high reliability in detecting cardiac arrhythmias and in preventing undue issuances of defibrillating pulses. To attain these objectives, the implantable defibrillator includes a probability density function (PDF) analysis circuit 28 such as is described in incorporated U.S. patent application Ser. No. 175,670, U.S. Pat. No. 4,184,493 and U.S. Pat. No. 4,202,340, mentioned above. Furthermore, the implantable defibrillator includes a rate analysis and averaging circuit 30 which senses, analyzes, and averages a rate signal indicative of ventricular contractions of the heart 10. When the circuits 28 and 30 detect abnormal cardiac rhythms, they each assert an enabling signal which together energize an AND gate 32 which asserts an INVST signal, which in turn, initializes a high-voltage inverter and control circuit 34 in preparation for delivering a defibrillating pulse to the patient's heart. Each such pulse passes to the heart across electrodes 20 and 22.

The delivery of the defibrillating pulse, though, does not occur unless the circuit 34 has been placed in an active state. To place it in an active state, the ring magnet 21 is used to toggle the status flip-flop 26 so that it asserts an EN signal at the Q output thereof and supplies it to the circuit 34 to enable the inverter and control circuit 34. Further, a signal over conductor 35 from the rate circuit 30, being synchronized with the occurrence of a ventricular contraction signal of the heart 10, provides a timing signal to the circuit 34 so that the issuance of defibrillating pulses are synchronized with a ventricular contraction. When so synchronized, the defibrillating pulse is most effective to defibrillate the heart 10, and to reduce the likelihood of accelerating the arrythmia.

To keep track of the number of defibrillating pulses issued, the circuit 34 produces a CT pulse signal each time it issues a defibrillating pulse. The CT pulse signal is used by pulse counting circuitry, subsequently explained.

Still referring to FIG. 1, a comparator 36 associated with the rate circuit 30 sets the beat rate threshold, for example at 160 beats per minute, at which rate the circuit 30, in conjunction with the PDF output via AND gate 32, asserts an enabling signal to initialize the h.v. inverter circuit 34. The rate analysis and averaging circuit 30 generates on conductor 31 an analog RATE signal having a magnitude representative of the ventricular rate and supplies it to one terminal of the comparator 36. A RATE THRESHOLD signal is applied to the other terminal of the comparator 36. During manufacture of the defibrillator, the voltage level of the RATE THRESHOLD signal is set so that the comparator 36 energizes the AND gate 32 when the ventricular beating rate, as indicated by the RATE signal, reaches the predetermined triggering magnitude of, say 160 beats per minute.

Should an actual fibrillation of the heart occur and the inverter issue a defibrillating pulse, a digital pulse counter, comprising register 38, responds to the CT pulse signal generated by the inverter circuit 34. The counter 38 thus keeps a running count of the number of defibrillating pulses issued. Upon demand, this count information can be electromagnetically transmitted during a "magnet test", as will be explained below. When the device is in the active state, the magnet test is initiated by momentarily placing the ring magnet 21 over the reed switch 24 and then removing the magnet. In response, the inverter starts running and a Telemetry Control signal from the magnet test logic 40 enables converter 39 to serialize the digital count information, and to transform the serial data bits to a pulse-width-modulator circuit 90 which frequency modulates the frequency of the high-voltage inverter via the frequency modulator 92. When the inverter is running, RF is generated by the inverter coil which is detected outside the body by the demodulator 12. By demodulating and detecting the RF frequency, the storage capacitor charge time is detected (corresponding to the maximum time that the RF is present) as well as the total number of defibrillator pulses delivered to the patient. The demodulator circuit 12 is a conventional FM demodulator and detector. It is located preferably within a few inches of the patient. When demodulated, the circuit 12 displays capacitor charge time, indicating the condition of the implanted battery, and displays the accumulated number of pulses issued by the defibrillator.

Status Indication and Change

Certain audio sounds emitted by the audio oscillator 50 and piezoelectric transducer 52 indicate the state of the implantable defibrillator. In the active state, the status flip-flop 26 of FIG. 1 holds enabled one input of an AND gate 44, the other input thereof being periodically enabled by ventricular beating signals from the rate circuit 30. Thus, when the magnet 21 is placed near the reed switch 24, the occurrence of each ventricular beating pulse from the rate circuit 30 momentarily energizes the AND gate 48 and an audio oscillator 50. (When reed switch 24 is closed by magnet 21, a low or "0" state is provided to inverter 46, and a "1" input is provided to AND gate 48.) The oscillator 50 then drives an acoustical speaker (piezoelectric transducer) 52 coupled directly to the case of the implantable defibrillator. So, when residing in the active state, e.g., status flip-flop 26 asserting its Q output, sounds synchronous with the heart beat are periodically emitted. In the preferred embodiment, the piezoelectric transducer 52 resonates at about 3,000 Hertz and is aurally detected by a person within range of the sound emitted by the transducer. Thus, pulsed tones emitted by the piezoelectric crystal 52 synchronous with the heart beat indicate that the bipolar electrode 18 is properly positioned within the heart of the patient.

On the other hand, if the status flip-flop 26 is in the inactive state, e.g. EN signal deasserted, the AND gate 44 is disabled and flip-flop 26 provides, through its $\overline{Q}$ output, a continuous enabling signal to one input of the AND gate 48. In the inactive state, placement of the magnet 21 near the reed switch 24 also provides, through inverter 46, a continuous enabling signal to the other input of AND gate 48. The result is that the oscillator 50 is continuously driven to provide a steady-state audible tone from the piezoelectric transducer 52, of approximately 3000 Hz.

Thus, a pulsed tone indicates that the defibrillator is active, and a continuous tone indicates that it is inactive.

When the device is in the active state, if the bipolar sensing probe 18 is not properly positioned within the right ventricle, no tones at all will be emitted as the ventricular signals are not being sensed. Thus, the presence or absence of an audible tone indicates whether the probe 18 is properly lodged about the right ventricle.

The frequency of operation of the oscillator 50 and piezoelectric transducer 52 is chosen to be substantially equal to the natural resonant frequency of vibration of the rigid case which encloses the defibrillator circuits so that the transducer 52 consumes a minimum amount of energy for a given level of audio emissions.

Figure 7:
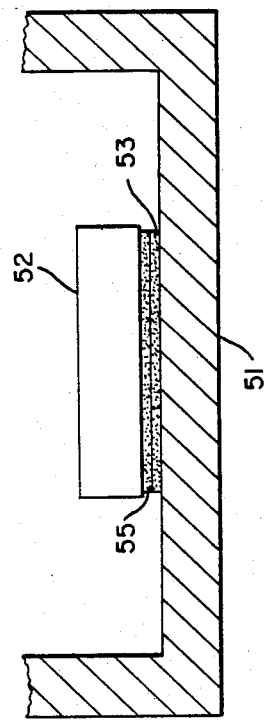
FIG. 7 shows the mounting arrangement of a piezoelectric crystal on the wall of a case enclosing the implantable components of FIG. 1.

The mounting of the piezoelectric crystal on an inner wall 51 of the implanted case is depicted in FIG. 7. To efficiently resonate the wall 51 of the case, a solid layer 53 of epoxy cement, such as Eccobond 24 adhesive, serves as a bonding medium between a surface of the crystal 52 and the surface of the wall 51 via an insulating tape 55. Preferably, no air cavity between the crystal and the wall exists to generate the audible emissions. Rather, the wall 51 itself vibrates to generate the sound.

State changes of the defibrillator (by status flip-flop 26) are accomplished by holding the magnet in place over the reed switch more than a predetermined time period, which in the preferred embodiment, is thirty seconds. To change the state, a 30-second timer circuit 54 produces a CK signal which toggles the status flip-flop 26 when the magnet 21 is held in place (reed switch 24 closed) for more than thirty seconds. The timer 54 preferably comprises an R-C charging network in a triggering circuit to produce the CK signal. Any suitable timer, such as a digital timer responsive to the reed switch, could be employed as a delay timer. When in the inactive state, status flip-flop 26 also effects opening of the power circuits to all non-essential components of the defibrillator to reduce current drain from the batteries (not shown). While being in the inactive state, only the status change and audio indicating circuits need power. Similarly, when in the active state, the EN signal enables an electronic switch (not shown) to provide electrical power to the rate circuit 30 and PDF circuit 28.

Rate Analysis and Averaging Circuit 30

Figure 2:
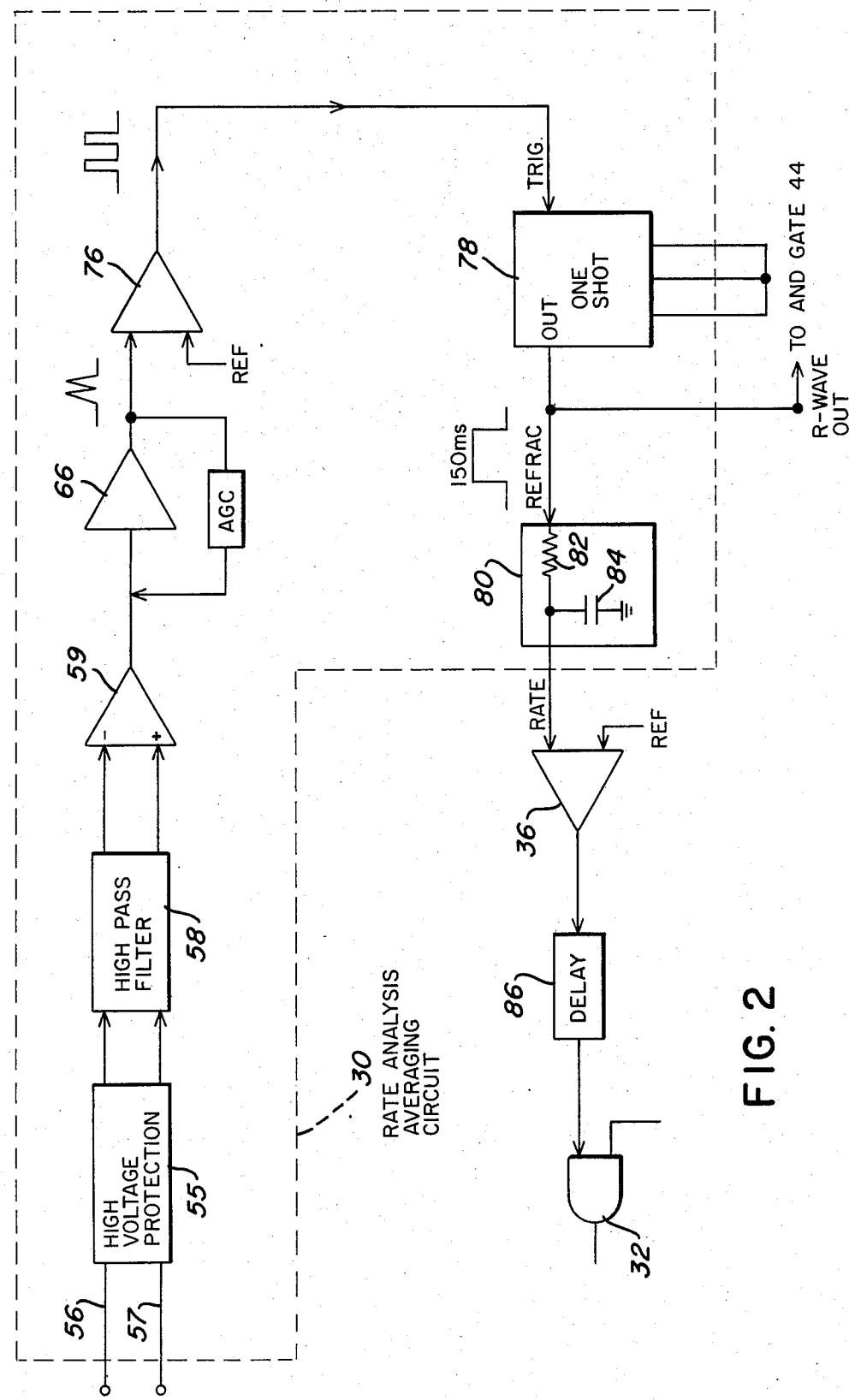
FIG. 2 is a detailed circuit diagram of the rate analysis and averaging circuit of FIG. 1.

FIG. 2 is a circuit diagram of the rate analysis and averaging circuit 30 of FIG. 1. As previously stated, the circuit 30 senses depolarizations of the right ventricle and, in response thereto, generates an analog signal having a voltage level proportional to the average ventricular beating rate. In the circuit 30, a pair of conductors 56 and 57 receive ventricular signals from the bipolar sensing probe 18. The ventricular beating signal then passes to a high pass filter 58 which attenuates signal components below a frequency of 30 Hz. Thereafter, pre-amplifier 59 amplifies the signal from the high pass filter. A high voltage protection circuit 55 is interposed between the electrode 18 and the high pass filter 58 to protect the circuit from high voltage resulting from a defibrillating pulse.

The pre-amplifier 59 is connected with amplifier 66 having an automatic gain control (AGC) in the feedback cirouit. The AGC tries to maintain a constant amplitude output with varying input signal levels. ECG input signals are known to vary dramatically in amplitude.

A pulse shaping circuit comprising a comparator 76 receives the gain controlled ventricular beating signal and generates in response thereto a series of square-wave pulses. Advantageously, both the positive and negative swings of the ventricular beating signal produce triggering pulses, and thus the circuit 30 responds equally well to various characteristic ventricular signals associated with patients who have either a strong positive or negative ventricular signal, or to characteristic signals derived from various locations about the ventricle about which the bipolar sensing probe 18 may be positioned. For this reason and others, the circuit 30 is very reliable.

The square-wave pulses from comparator 76 trigger a one-shot multivibrator 78 which produces another square-wave pulse of a fixed duration of approximately 150 milliseconds, preferably. This period represents the refractory period of the device. During this 150 milli-second refractory period, the multivibrator 78 cannot be re-triggered by other signals, such as T-waves, etc., until the period has expired. The REFRAC signal comprising uniform-width refractory pulses from the multivibrator 78 is then fed to both an averaging circuit 80 and the AND gate 44 (FIG. 1). In addition, the R-wave output signal is provided, via line 35, to the high-voltage inverter control circuit 34 to synchronize defibrillation pulses with the R-wave output (see FIGS. 1 and 3). The rate averaging circuit 80, comprising a resistor 82 and a capacitor 84, integrates the REFRAC signal from the multivibrator 78. The circuit 80 is similar in operation to a frequency-to-voltage converter. At sixty beats per minute, for example, the REFRAC signal has a duty cycle of 15%. When integrated, i.e. averaged, it produces the aforementioned RATE signal of a pre-determined magnitude. As the beating rate increases, the duty cycle of the REFRAC signal also increases as the constant-width pulses occur more often and, when integrated, the circuit 80 produces the RATE signal of a correspondingly higher magnitude. The RATE signal is compared with a RATE THRESHOLD signal by the comparator 36 (also shown in FIG. 1) which generates the enabling signal for energizing the AND gate 32. The RATE THRESHOLD signal of comparator 36 is selected so that the comparator produces the enabling signal at a predetermined rate.

Although not shown in FIG. 1, a delay 86 interposes a two-second delay and only passes a signal to the AND gate 32 if the input to the delay 82 is maintained for 2 sec. or more. This delay reduces the likelihood of detecting short, self-terminating arrythmias.

HIGH-VOLTAGE INVERTER AND CONTROL CIRCUITS

Figure 3:
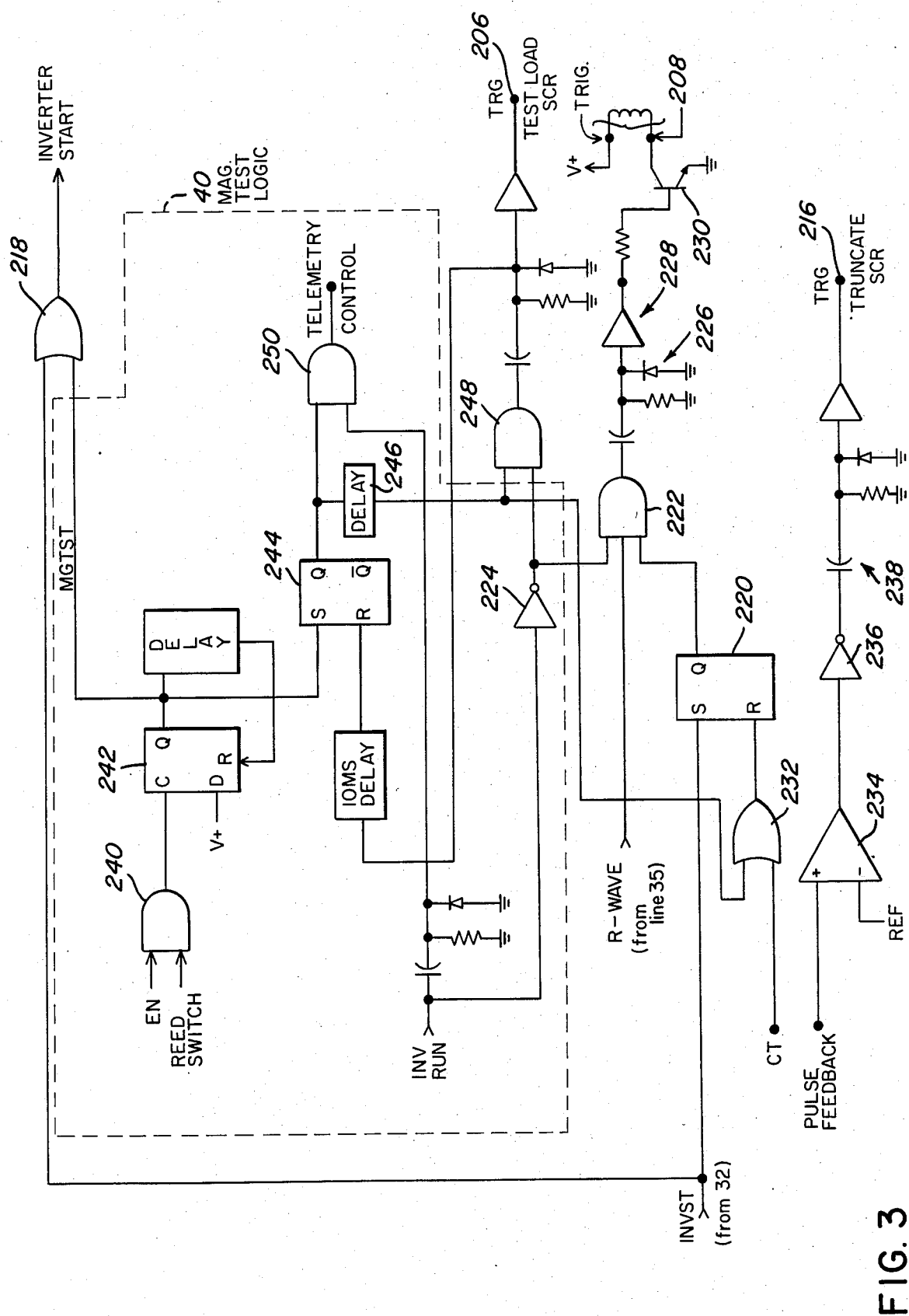
FIG. 3 is a schematic circuit diagram of the magnet test logic and inverter control circuit of FIG. 1.
Figure 4:
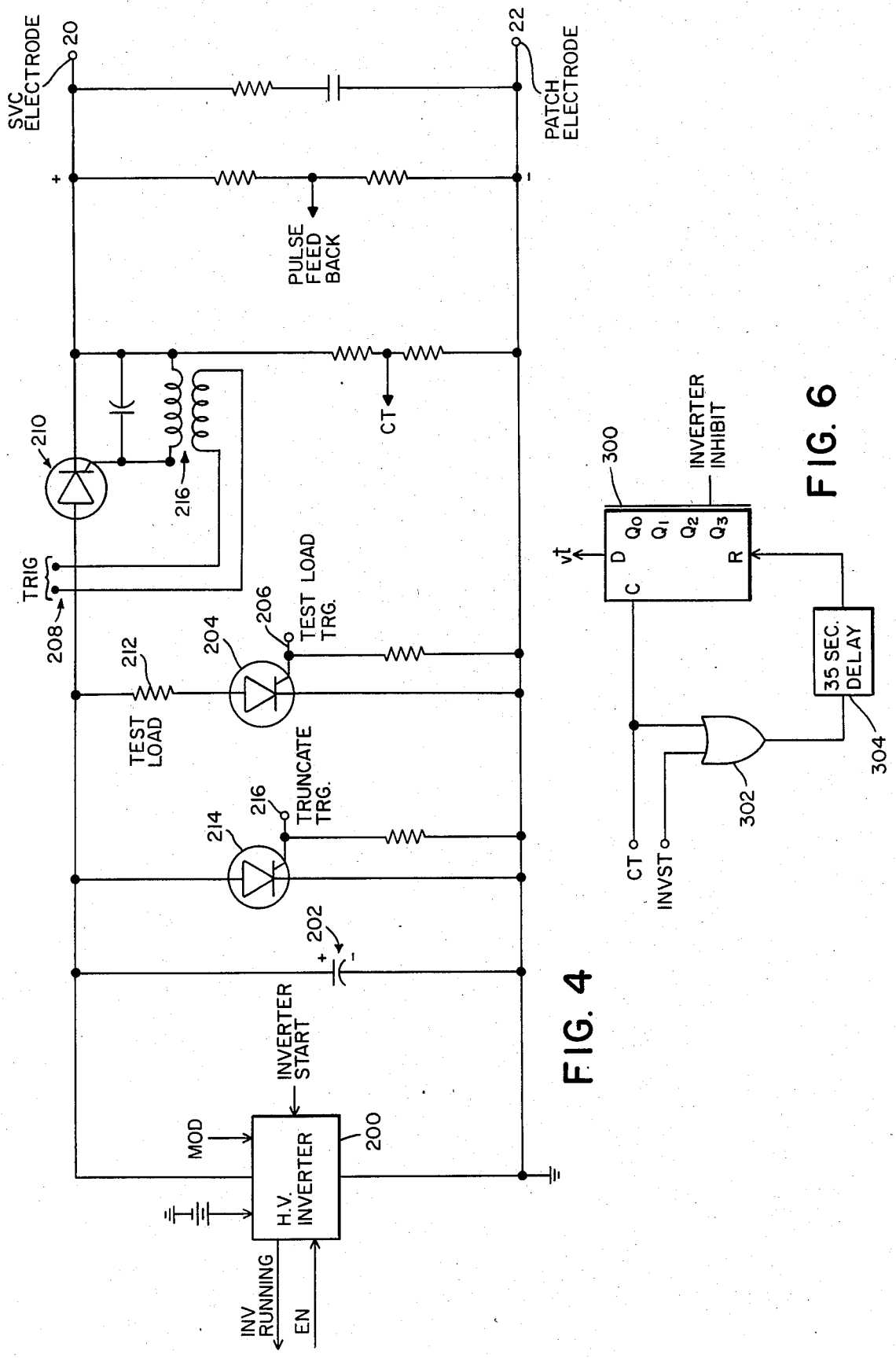
FIG. 4 depicts a partial circuit diagram of the inverter control circuitry of FIG. 1.

The high-voltage inverter and control circuit 34, along with the magnet test logic circuit 40, is shown in greater detail in FIGS. 3, 4 and 6. Turning first to FIG. 4, the high-voltage inverter 200, also known as a DC-to-DC converter, is a conventional element well known in the implantable defibrillator art. Reference should be made, for example, to U.S. Pat. No. 4,164,946 which describes the DC-to-DC converter (element 30 in the '946 patent). The high-voltage inverter 200 charges an internal energy storage capacitor 202 which is charged to a predetermined level and is discharged either across the heart of the patient via the SVC electrode 20 and patch electrode 22, or is discharged through a test load resistor 212 under conditions as will be described below. The high-voltage inverter 200 includes an implanted coil (not shown) which emits RF signals during the operation of the inverter, i.e., during the charge time of the capacitor 202. It is this RF emission that is detectable outside the body of the patient in a manner to be described.

When the high-voltage inverter is enabled, by the EN signal from status flip-flop 26 (described above), the inverter 200 is in condition for operation. The high-voltage inverter 200 begins operation upon receipt of an INVERTER START signal which, as shown in FIG. 3, is initiated by receipt of either an INVST signal from the AND gate 32 or an MGTST signal from the magnet test logic circuit 40 (as shown in FIGS. 1 and 3). The high-voltage inverter begins running and provides an INV RUNNING signal to the magnet test logic circuit 40, in a manner to be described below. The high-voltage inverter keeps running until the energy storage capacitor 202 is charged to its predetermined level. It should be apparent that the period of time that the high-voltage inverter is running, i.e., the period of time it takes to charge the capacitor 202, is an indication of the defibrillator battery strength. (See, the description in U.S. Pat. No. 4,164,946.) Further, during the charge time of the high-voltage inverter, the RF emissions of the inverter coil are frequency modulated to represent the number of inverter discharges across the electrodes 20, 22, which information is detectable outside the body of the patient by the demodulator and decoder 12.

The capacitor 202 is discharged either through the test load 212 or across the patient electrodes 20 and 22 dependent upon receipt of a trigger pulse either to the test load SCR 204, via line 206, or a trigger signal across leads 208, which enables the patient SCR 210. Line 206 and leads 208 are actuated by control circuitry as will be described further below in connection with FIG. 3. When SCR 204 is triggered via a pulse on line 206, the capacitor 202 discharges across the test load resistor 212; when patient SCR 210 is actuated, via signals over leads 208, the capacitor 202 discharges across the patient electrodes 20, 22. When the capacitor discharges across the patient electrodes, a count signal, at CT, is provided which, as shown in FIG. 1, increments the counter 38 representing the number of discharges across the patient's heart. Similarly, a pulse feedback signal, as shown in FIG. 4, is provided which is sent to control circuitry as shown in FIG. 3 for triggering the truncate SCR 214, as will be described.

The patient SCR 210 is triggered by signals across the leads 208, via an anti-shunt circuit. The anti-shunt circuit includes a small pulse transformer 216 connected to the patient SCR 210 for triggering same in response to a trigger input across leads 208. The trigger input signal is applied to the primary winding of transformer 216 and the secondary winding of the transformer activates the patient SCR 210 permitting the high-voltage defibrillation pulse to pass to the SVC and patch electrodes, 20 and 22. Such a circuit avoids the drawback that when an external defibrillation voltage is applied to the heart of the patient having an implanted device connected to the patient's heart, the external defibrillation voltage will not pass through the implanted device and specifically through the high-voltage inverter. The transformer coupling eliminates a low impedance path to ground.

The truncate SCR 214 is activated by a signal on line 216, as shown in FIGS. 3 and 4. The purpose of the truncate SCR is as follows. When the capacitor 202 discharges across the implanted electrodes, the discharge is an exponentially decaying waveform. When the waveform decays to a certain voltage, the truncate SCR 214 is fired to truncate the decaying pulse. Preferably the predetermined point of decay is approximately ⅔'s of what a fully decayed pulse would otherwise look like.

The triggering signals to the circuit of FIG. 4 are provided by the inverter control circuitry, in conjunction with the magnet test logic circuitry 40, as shown in FIG. 3. As shown in FIG. 3, receipt of an INVST signal from AND gate 32 or receipt of a MGTST signal from magnet test logic circuit 40, is applied to OR gate 218 which provides an INVERTER START signal to initiate the high-voltage inverter to charge the charging capacitor 202. Assuming a need for defibrillation occurs, resulting in an INVST signal from AND gate 32, such signal starts the inverter running, via OR gate 218, and sets a patient flip-flop 220. The patient flip-flop output is applied to AND gate 222. A second input to the AND gate 222 is connected to the R-wave detected output signal (over line 35) from the rate analysis circuit 30 as shown in FIG. 1. The third input to the AND gate 222 is coupled with the high-voltage inverter to receive the INV RUNNING signal via inverter logic element 224. During the time that the inverter is running, the third input to the AND gate 222 is low and the output of the AND gate 222 is low. When the inverter stops running, i.e., at the completion of the charging of the defibrillator capacitor, the inverter logic element 224 output is high. Thus, subsequent R-wave inputs to the AND gate 222 cause a pulse to be emitted, through a suitable RC pulse shaping network 226 and buffer 228 to a transistor 230. The transistor 230 is actuated and a patient trigger pulse is applied over leads 208. As previously described, the receipt of a patient trigger pulse over leads 208 fires the patient SCR 210, as shown in FIG. 4, and the capacitor 202 discharges across the electrodes connected to the patient's heart. This discharge also provides a count CT pulse which resets the patient flip flop 220 via OR gate 232.

When the patient SCR 210 is triggered, the capacitor 202 discharges to provide a high-voltage exponentially decaying pulse across the electrodes connected to the patient's heart. This exponentially decaying pulse is fed back, via pulse feedback terminal to a threshold comparator 234. When the exponentially decaying pulse feedback signal drops to a predetermined reference level, as provided to the negative input terminal of comparator 234, the comparator provides an output which is inverted by inverter 236, shaped by pulse shaping network 238, and a pulse is provided at lead 216 to fire the truncate SCR 214 as shown in FIG. 4. When the truncate SCR 214 is fired, the exponentially decaying pulse across the electrodes 20, 22 is truncated. This is done because it is undesirable to require the pulse to exponentially decay to a zero level.

The operation of the magnet test logic circuit 40 and the triggering of test load SCR 204 will no be described. The magnet test logic circuit is initiated when AND gate 240 is asserted. AND gate 240 is asserted when the defibrillator is enabled, i.e., receipt of an EN input from status flip-flop 26, and the magnet 21 is removed from the reed switch 24 to provide a positive, or high, signal to the AND gate 240. That is, when the magnet 21 is brought into close proximity to the reed switch 24, thus closing the reed switch contacts, a negative or zero input is provided to the AND gate 240. Upon removal of the magnet, thus opening the reed switch 24, the input to AND gate 240 from the reed switch becomes high thus asserting the AND gate 240. It should be noted that the magnet 21 must be removed from proximity to the reed switch 24 in less than 30 seconds to cause a magnet test to be initiated. If the magnet 21 is in proximity to the reed switch 24 for greater than 30 seconds, then the status flip-flop 26 is disabled and the input to AND gate 240 from the status flip-flop 26 is low, thus preventing assertion of the AND gate 240.

Assertion of the AND gate 240 sets delay flip-flop 242 which provides a MGTST signal to the inverter and control circuit 34 via OR gate 218, thus starting the inverter. Further, the flip-flop 242 output sets a magnet test flip-flop 244. Setting of magnet test flip-flop 244 results in an input signal, after a brief delay by delay element 246, to AND gate 248. A second input to AND gate 248 is connected to the INV RUNNING line via inverter logic element 224. When the inverter has completed running, thus reflecting that the internal capacitor 202 is completely charged, the second input to AND gate 248 goes high and the AND gate 248 is asserted. Output pulse from AND gate 248 is provided to the test load SCR trigger line 206, via pulse shaping and buffer circuits, and the test load SCR 204 is fired. The capacitor then discharges across the test load resistor 212.

It should also be noted that when the magnet test flip-flop 244 is set and its Q-output is high, the Q-output is also provided to OR gate 232 to keep the patient flip-flop 220 in a reset condition. Thus, during a magnet test condition, the patient flip-flop is prevented from operation and no defibrillating pulses across the patient's heart can be emitted.

During a magnet test, when the magnet test flip-flop 244 is set, telemetry control AND gate 250 is enabled during the time that the inverter is running. This provides a telemetry control signal from the magnet test logic 40 which signal is provided to the 8-bit parallel-to-serial converter 39, as shown in FIG. 1.

As previously discussed, the number of defibrillating shocks administered to the patient results in CT signals which are applied to counter 38, as shown in FIG. 1. When the telemetry control signal from the magnet test logic 40 is issued, the contents of the counter 38 are provided to the 8-bit parallel-to-serial converter 39. The serial data bits from the converter 39 are provided to pulse width modulation circuit 90 which in turn provides a pulse width modulated signal to the inverter frequency modulator 92. The inverter frequency modulator 92 frequency modulates the RF signal emitted by the inverter coil during the time th inverter is running. This frequency modulated information is detectable outside the body of the patient by the external demodulator and decoder 12 which demodulates the frequency modulated signals to display the number of defibrillation pulses that have been counted. Further, by detecting the period of time that the inverter coil is emitting radio frequency, the charge time of the defibrillator capacitor is determined. It should be noted that, whereas it takes approximately 2 seconds for telemetry information to be read from the counter 38, converted, pulse width modulated, and inverter frequency modulated, in contrast, it takes 5–6 seconds for the high voltage capacitor contained within high voltage inverter and control circuit to charge up.

The demodulator and decoder 12 and display 14 may be any suitable external device suitable for demodulating, decoding and displaying the transmitted information.

Turning now to FIG. 6, the 4-count hold circuit is disclosed. As previously discussed, the 4-count hold circuit inhibits the inverter after four defibrillating pulses are applied to the patient until after 35 seconds of normal sinus rhythm is detected. The 4-count hold circuit includes a four-stage shift register with an inverter inhibit line provided to the fourth Q3 stage. As defibrillating pulses are detected over the CT input, each CT pulse representative of a defibrillating shock is counted. Upon receipt of four counts, the inverter inhibit output is asserted to inhibit the high-voltage inverter. Receipt of each CT pulse is also provided, via OR gate 302 to a 35-second delay timer 304. Receipt of each CT input starts the 35-second delay timer running. If, after four CT pulses, the INVST input to OR gate 302 is still receiving inputs, reflecting the fact that the patient is still in need of defibrillation, the 35-second delay timer keeps running. Only when normal sinus rhythm is detected, i.e., by absence of the INVST signal, does the 35-second delay timer reset the shift register 300 thus enabling the high-voltage inverter to operate.

BIPOLAR SENSE ELECTRODE 19

Figure 5:
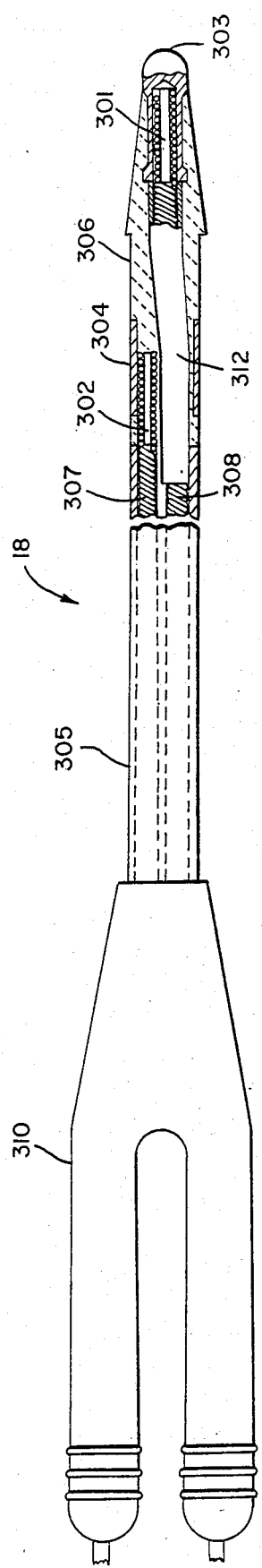
FIG. 5 depicts the structural details of the bipolar sensing probe of FIG. 1 for sensing electrical signals of the patient's heart.

FIG. 5 depicts the details of the bipolar sense electrode 18 shown in FIG. 1. The electrode 18 is implanted in the right ventricle and, as previously mentioned, senses relatively weak electrical signals produced by ventricular contractions. This signal, known as the R-wave, is then supplied to the rate analysis and averaging circuit 30 of FIG. 1.

The electrode 18 consists of a first wire lead 301 and a second wire lead 302 spaced apart from the lead 301. The lead 301 electrically communicates with a conductive distal tip 303 which is crimped around the lead 301, while the lead 302 electrically communicates with a conductive ring electrode 304 in contact therewith and encircling a flexible insulating elastomer 306. In the preferred embodiment, the spacing between conductive elements 303 and 304 is about one centimeter.

Lead coils 307 and 308 are wrapped around and encircle the wire leads 301 and 302. The lead coils 307, 308 are separately enclosed in bilumen tubing 305 and extend into a plug element 310 for plugging into the implantable device. Lead coil 308 further includes an encircling medical grade silicone tubing 312 near the distal end.

It should be apparent that the exact construction of the bipolar electrode 18 may vary from that described above, the important feature being the spaced distance between the distal tip 303 and the ring 304 electrodes. Moreover, the two electrodes may be separate electrodes, such as corkscrew type or needle type electrodes that are not part of a unitary structure. It has been determined that by limiting the distance between the tip 303 and ring 304 to between 0.5 and 1.5 centimeters, and preferably 1.0 centimeter, rather than a distance exceeding 2.5 centimeters, as normally provided by electrodes in prior art pacing devices, a signal characterized by faster rise times more useful for rate counting, particularly during chaotic cardiac arrhythmias such as polymorphic ventricular tachycardia and ventricular fibrillation can be obtained.

It should be noted that as used herein, the terms "fibrillation", "cardioversion", "defibrillation", "defibrillator" and "cardioverter" are intended to refer to all arrhythmias of a life-threatening nature that can be reverted to normal sinus rhythm by the application of high-voltage countershock, and the reversion of such arrhythmias to normal sinus rhythm; life-threatening high rate tachycardia, for example, should be construed as equivalent to "fibrillation" as used herein.

We have set forth an illustrative embodiment of our invention wherein we attain the above mentioned objectives. It is apparent that certain features and aspects of the invention may be constructed and/or practiced in a manner that is not specifically shown or described; however, we intend by the appended claims that all such modifications and variations which can be made by those skilled in the art may come within the scope of our invention as defined.

What is claimed is:

1. An implantable defibrillation system for automatically defibrillating the heart of a patient comprising:
   detecting means for detecting fibrillation of the heart;
   defibrillation means responsive to said detecting means for generating and applying to said heart at least one high-energy defibrillating pulse, said defibrillating means including a storage capacitor and a high voltage inverter means for charging said storage capacitor, said high voltage inverter means capable of emitting radio frequency (RF) signals during the charging of the storage capacitor, said RF signals capable of being detected externally of the patient;

counting means responsive to said defibrillating means for maintaining defibrillating pulse count information and for providing the pulse count information to a telemetry means;

telemetry means connected to said counting means and said high voltage inverter means for receiving the pulse count information and for transmitting information signals indicative of said pulse count information externally of the patient, wherein said telemetry means includes frequency modulation means for frequency modulating the RF signals emitted by said inverter means during the charging of said storage capacitor in accordance with the pulse count information, said telemetry means being responsive to a telemetry control signal to transmit said information signals;

control means for receiving an activation signal generated externally of the patient and, in response to said activation signal, for providing an inverter start signal to said high voltage inverter means to initiate the running of said inverter means and to discharge said storage capacitor upon completion of the running of the inverter means, and to provide a telemetry control signal to said telemetry means; and external activation means for generating an activation signal external of the patient.

2. The implantable defibrillation system of claim 1, wherein said counting means comprises a register means for counting the number of defibrillating pulses applied to the heart of a patient and wherein said telemetry means includes serial converting means coupled with said register means for converting the number of pulses maintained in the said register means to a serial stream of pulses, said telemetry means further including pulse width modulation means for pulse width modulating the serial stream of pulses from said serial converting means, said pulse width modulation means coupled with said frequency modulation means wherein said frequency modulation means frequency modulates the RF signals emitted by said high voltage inverter means in accordance with the pulse width modulating signal from said pulse width modulating means.

3. The implantable defibrillation system of claim 2, wherein said serial converting means includes means for receiving said telemetry control signal from said control means.

4. The implantable defibrillation system of claim 1, wherein said control means further includes a test load resistor and means for discharging said storage capacitor across said test resistor upon completion of the running of said inverter means.

5. The implantable defibrillation system of claim 1, wherein said control means includes a reed switch responsive to a magnetic field activation signal and wherein said external activation means includes means for generating a magnetic field activation signal.

6. An implantable defibrillation system, including an electrode positionable in the ventricle of the heart of a patient for detecting R-waves, and a high voltage inverter means for charging a defibrillator storage capacitor, the system comprising, an implantable audio oscillator means for generating audio tones that are aurally detectable outside the body of a patient;

enabling circuit means having an enable and disable status output coupled with said high voltage inverter means for enabling and disabling the high voltage inverter means;

R-wave detecting means coupled with said electrode for detecting the R-waves of a patient's heart;

logic means coupled with said audio oscillator means and each of said enabling circuit means and said R-wave detecting means for providing control signals to said audio oscillator means indicative to the proper positioning of the electrode within the heart of a patient and indicative of the enable/disable status of the inverter means;

switch means responsive to an activation signal generated externally of a patient coupled with said enabling circuit means and said logic means to selectively enable and disable the high voltage inverter means and to enable the control signals from said logic means to control the audio tones emitted by the audio oscillator means.

7. The system of claim 6, wherein said logic means includes means for detecting the status output of said enabling circuit means and for receiving the detected R-waves from said R-wave detecting means and for providing, (1) a continuous control signal to said audio oscillator means when the enabling circuit means is in a disable status, (2) a periodic control signal to said audio oscillator means synchronized with the R-wave output of the R-wave detecting means when the enabling circuit means is in an enable status and R-waves are received from the R-wave detecting means indicating that the electrode is properly positioned within the heart of a patient, and (3) the absence of a control signal to said audio oscillator means when the enabling circuit means is in an enable status and no R-waves are received from the R-wave detecting means, indicating that the electrode is not properly positioned within the heart of the patient, whereby the audio oscillator means includes means for generating a continuous tone, a periodic tone, and no tone, in response to control signals (1)–(3), respectively.

8. The system of claim 6, wherein said switch means includes means for changing the status of said enabling circuit means between enable and disable status in response to an activation signal maintained beyond a predetermined time period.

9. The system of claim 6, wherein said audio oscillator means includes a piezoelectric transducer affixed directly to the casing of the implantable defibrillator.

10. An implantable defibrillation system for automatically defibrillating the heart of a patient comprising:

bipolar electrode means implantable in a heart ventricle for sensing ventricular contractions, comprising a pair of electrodes spaced apart between 0.5 cm and 1.5 cm;

detecting means connected with said bipolar electrode means for detecting the sensed ventricular contractions and for providing a heart beat pulse signal proportional to each detected ventricular contraction, and for providing an arrhythmia signal when the detected ventricular contractions exceed a predetermined rate;

defibrillating means connected with said detecting means for providing a defibrillating pulse to the heart of a patient, said defibrillating means including means for charging an internal storage capacitor to a predetermined voltage level upon receipt of said arrhythmia signal, and means for discharging the voltage stored in said storage capacitor across the heart of a patient synchronous with said heart beat pulse signal.

11. An implantable defibrillation system as claimed in claim 10 wherein said detecting means comprises, Processing means for converting the sensed ventricular contractions into a series of uniform heart beat pulse signals proportional to each ventricular contraction, said processing means including an automatic gain control amplifier, averaging means for averaging the number of heart beat pulse signals per unit of time and providing an analog output signal having a magitude proportional thereto, said averaging means including means for converting the frequency of the uniform pulses to a voltage output signal, and, threshold means for comparing the voltage output signal with a reference signal and providing an arrhythmia signal when said voltage output signal exceeds the level of said reference signal.

12. An implantable defibrillation system as claimed in claim 11 wherein said pair of electrodes are separated by a distance of one (1) cm.

13. An implantable defibrillation system as claimed in claim 12 wherein said pair of electrodes are mounted on an elongated probe, one electrode mounted at the distal tip of said probe, the other electrode comprising a ring electrode circumferentially surrounding the probe and spaced from said distal tip.

14. An implantable defibrillation system for automatically defibrillating the heart of a patient comprising:

bipolar electrode means implantable in the ventricle of a heart for sensing ventricular contractions;

rate analysis circuit means connected with said bipolar electrode means for detecting the sensed ventricular contractions and for providing, (1) an analog rate output signal having a magnitude proportional to the average number of ventricular contractions per unit of time, and (2) a heart beat pulse signal proportional to each detected ventricular contraction;

threshold means connected with said rate analysis circuit means for receiving said analog rate output signal and for providing a threshold output signal when said analog rate output signal exceeds a predetermined reference level;

high voltage inverter means for receiving said threshold output signal, for charging a storage capacitor to a predetermined voltage level upon receipt of said threshold output signal, and for providing an inverter output signal when the storage capacitor is fully charged;

a storage capacitor connected with said high voltage inverter means for receiving a voltage charge, said storage capacitor coupled with implantable defibrillating electrodes;

logic means connected with said rate analysis circuit means and said high voltage inverter means for receiving said heart beat pulse signal and said inverter output signal and for providing a discharge signal in response to receipt of said heart beat pulse signal and inverter output signal;

discharge means connected with said storage capacitor and said logic means for discharging said storage capacitor across the implantable defibrillating electrodes in response to receipt of said discharge signal.

15. An implantable defibrillation system as claimed in claim 14 further comprising PDF processing means connectable to the heart for receiving EOG waveforms and for processing said EOG waveforms in accordance with a probability density function to provide a probability density function output signal, and wherein said high voltage inverter means includes means for receiving said probability density function output signal and for providing said inverter output signal upon receipt of said probability density function output signal and said threshold output signal.

16. An implantable defibrillation system as claimed in claim 14 wherein said bipolar electrode means comprises a pair of electrodes spaced apart between 0.5 cm and 1.5 cm.

* * * * *